United States Patent [19]
Panagiotou et al.

[11] Patent Number: 6,143,370
[45] Date of Patent: Nov. 7, 2000

[54] PROCESS FOR PRODUCING POLYMER COATINGS WITH VARIOUS POROSITIES AND SURFACE AREAS

[75] Inventors: Thomai Panagiotou, Chelsea; Yiannis Levendis, Boston, both of Mass.

[73] Assignee: Northeastern University, Boston, Mass.

[21] Appl. No.: 09/140,611

[22] Filed: Aug. 26, 1998

Related U.S. Application Data

[60] Provisional application No. 60/057,703, Aug. 27, 1997.

[51] Int. Cl.[7] .................................................... B05D 1/02
[52] U.S. Cl. ................................ 427/422; 427/255.16
[58] Field of Search ............................... 427/255.6, 422

[56] References Cited

U.S. PATENT DOCUMENTS

| | | | |
|---|---|---|---|
| 4,828,882 | 5/1989 | Tsezos et al. | 427/213 |
| 4,954,371 | 9/1990 | Yializis | 427/44 |
| 5,269,980 | 12/1993 | Levendis et al. | 264/9 |

OTHER PUBLICATIONS

Levendis et al., "Combustion of Uniformly Sized Glassy Carbon Particles," Combust. Sci. and Tech., vol. 53, pp. 117–136, Jan. 1987.

Levendis et al., "Synthesis, Formation and Characterization of Micro–Sized Glassy Carbon Spheres of Controlled Pore Structure," Carbon, vol. 27, No. 2, pp. 265–283, Jan. 1989.

*Primary Examiner*—Shrive Beck
*Assistant Examiner*—Jennifer Calcagni
*Attorney, Agent, or Firm*—Weingarten, Schurgin, Gagnebin & Hayes LLP

[57] ABSTRACT

A process for forming polymer coatings on the surfaces of objects, e.g., medical stents, is disclosed. The coatings formed by the process of the invention comprise small spherical, spheroidal or irregular shape polymer particles, which may be adhered together. Coatings may have high porosity and high surface area. The process includes the steps of preparing a liquid feed solution of either mixtures of liquid organic monomers and polymerization catalysts which may optionally be pre-polymerized, or polymers dissolved in solvents; conducting the liquid feed solution into an aerosol generator; generating either a controlled or uncontrolled aerosol in the form of droplets; spraying the liquid feed solution from the aerosol generator into a thermal reactor on to the surface of an object; regulating the temperature and pressure of the reactor so that a portion of the solvent in the feed solution evaporates before the droplets are deposited on the object; and maintaining the spray of the liquid feed solution in the thermal reactor for an optimum period of time to allow the coating to form on the object. Optionally, another material, such as a drug, carbon black, calcium carbonate, etc., is added to the feed solution, as well. The experimental conditions are adjusted so that some of the solvent evaporates before the droplets hit the surface of the object. This can be done if the temperature of the surroundings is sufficiently high, the ambient pressure is significantly low, the residence time of the droplets is sufficiently long, or a combination of the above.

16 Claims, 12 Drawing Sheets

PROCESS FOR PRODUCING POLYMER COATINGS WITH VARIOUS POROSITIES AND SURFACE AREAS

This application claims benefit of provisional Application No. 60/057,703 Aug. 27, 1997.

CROSS REFERENCE TO RELATED APPLICATIONS

None

STATEMENT REGARDING FEDERALLY SPONSORED RESEARCH OR DEVELOPMENT

Not Applicable

BACKGROUND OF THE INVENTION

Past approaches to forming a coating on an object have included the technique of dipping the object into a polymer solution that will serve the coating when dried. With this technique, a coating with low surface area frequently forms. In addition, if the object to be coated is of irregular shape, the coating may not be uniform, since accumulation of polymer is frequently observed in the crevices of the object. A coating prepared in such a manner may break if the object is subjected to stress.

BRIEF SUMMARY OF THE INVENTION

The method of the invention provides a new process for the formation of polymer coatings on surfaces. The coatings formed by the process of the invention comprise small spherical, spheroidal or irregular shape polymer particles, which may be adhered together. Coatings may have high porosity and high surface area. The new process includes the steps of preparing a liquid feed solution of either mixtures of liquid organic monomers and polymerization catalysts which may optionally be pre-polymerized, or polymers dissolved in solvents; conducting the liquid feed solution into an aerosol generator; generating either a controlled or uncontrolled aerosol in the form of droplets; spraying the liquid feed solution from the aerosol generator into a thermal reactor on to the surface of an object; regulating the temperature and pressure of the reactor so that a portion of the solvent in the feed solution evaporates before the droplets are deposited on the object; and maintaining the spray of the liquid feed solution in the thermal reactor for a optimum period of time to allow the coating to form on the object. Optionally, another material, such as a drug, carbon black, calcium carbonate, etc., can be added to the feed solution, as well. The experimental conditions are adjusted so that some of the solvent evaporates before the droplets hit the surface of the object to be coated. This can be accomplished if the temperature of the surroundings is sufficiently high, the ambient pressure is significantly low, the residence time of the droplets is sufficiently long, or a combination of the above. Optionally, the steps of the process can be repeated so that a thicker coating is formed, or so that a different type of coating on the top of an existing coating is formed.

Coatings produced according to the process of the invention are more flexible and stronger than coatings produced in conventional ways. Also, the surface area of the coating can be varied at will in the process of the invention, either increased or decreased, to control the mass diffusion rates through the surface.

BRIEF DESCRIPTION OF THE SEVERAL VIEWS OF THE DRAWING

Other features and advantages of the invention will be apparent from the following description of the preferred embodiments thereof and from the claims, taken in conjunction with the accompanying drawings, in which:

DETAILED DESCRIPTION OF THE INVENTION

Figure 1A:
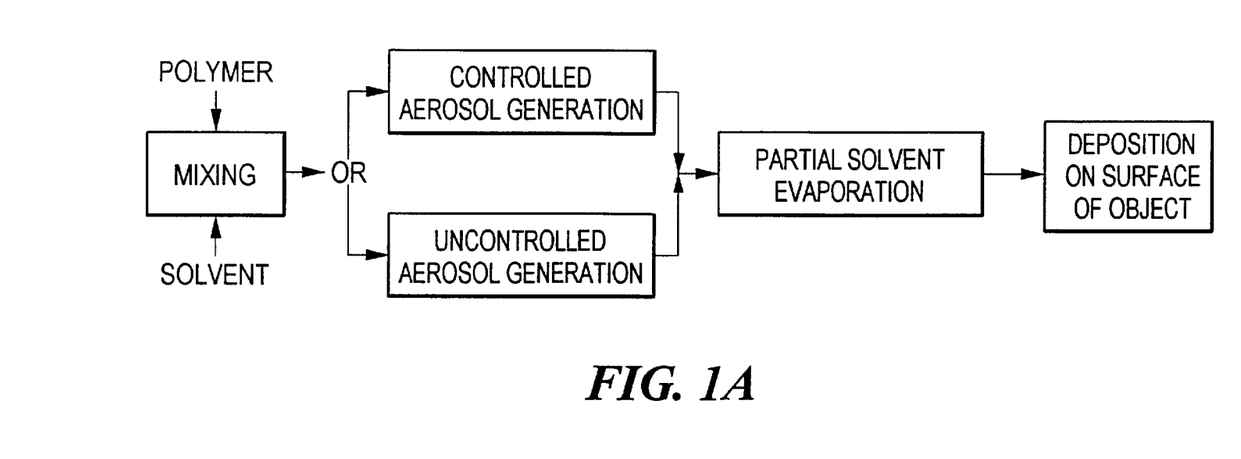
FIG. 1A is a flow diagram of the process of the present invention.
Figure 1B:
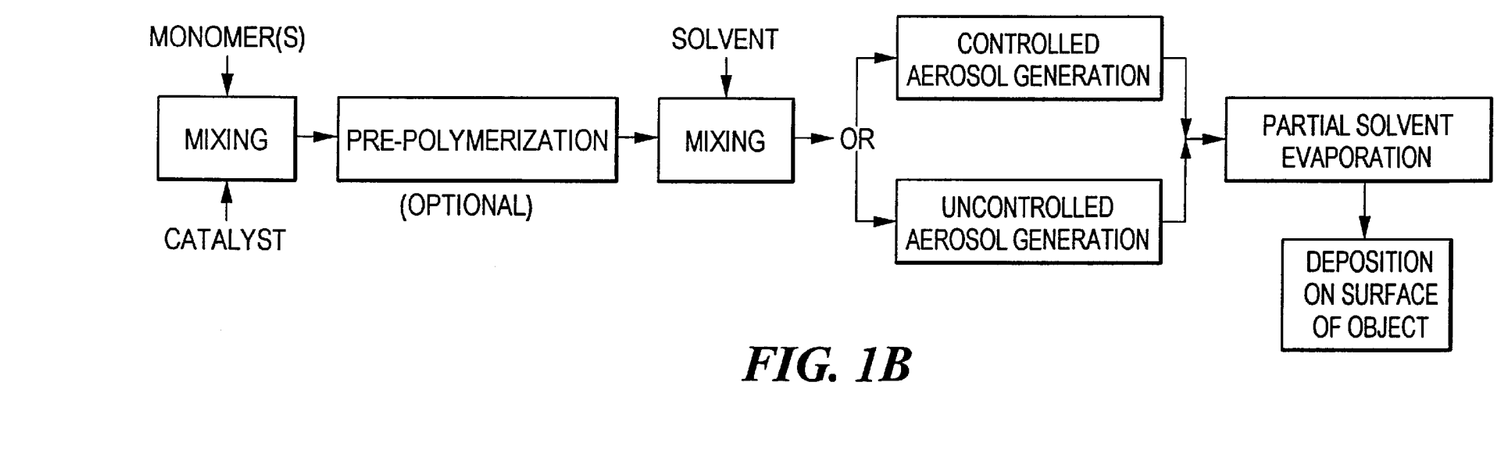
FIG. 1B is a flow diagram of a variation of the process of the present invention.

Referring to FIGS. 1A and 1B, a polymer coating is formed on the surface of an object in accordance with the process of the present invention, which comprises the steps of preparing a liquid feed solution of either mixtures of liquid organic monomers and polymerization catalysts which may optionally be pre-polymerized, or polymers dissolved in solvents; conducting the liquid feed solution into an aerosol generator; generating either a controlled or uncontrolled aerosol in the form of droplets; spraying the liquid feed solution from the aerosol generator into a thermal reactor on to the surface of an object; regulating the temperature and pressure of the reactor so that a portion of the solvent in the feed solution evaporates before the droplets are deposited on the object; and maintaining the spray of the liquid feed solution in the thermal reactor for a optimum period of time to allow the coating to form on the object.

In one embodiment (FIG. 1A), the liquid feed solution may comprise any polymer that can be completely dissolved in solvents. Examples of such polymers include but are not limited to poly(styrene), poly(methyl-methacrylate), poly(methyl-ethacrylate) acrylic resins, poly(-vinyl-acetate), poly(butadiene), poly(esters) (uncross-linked), formaldehyde resins, gelatins, proteins, poly-(ethylene-terephthalate) and poly(vinyl-chloride), dissolved in a suitable solvent such as toluene, acetone, benzene, acids, butanone, water, methanol, ethanol and hexane.

In another embodiment (FIG. 1B), the liquid feed solution may comprise liquid monomers including a polymerization catalyst or initiator dissolved in a suitable solvent. Suitable monomers include but are not limited to monomers of styrene, methyl methacrylate, acrylic acids, vinyl acetate, divinyl benzene or any liquid monomer or mixtures thereof whose polymerization can be achieved in bulk and can be readily controlled. The monomers may be mixed with a solution of polymerization initiator such as benzoyl peroxide, or potassium persulfate. Optionally, the monomers may be pre-polymerized in bulk and dissolved in a suitable solvent before being conducted to the aerosol generator.

Figure 2A:
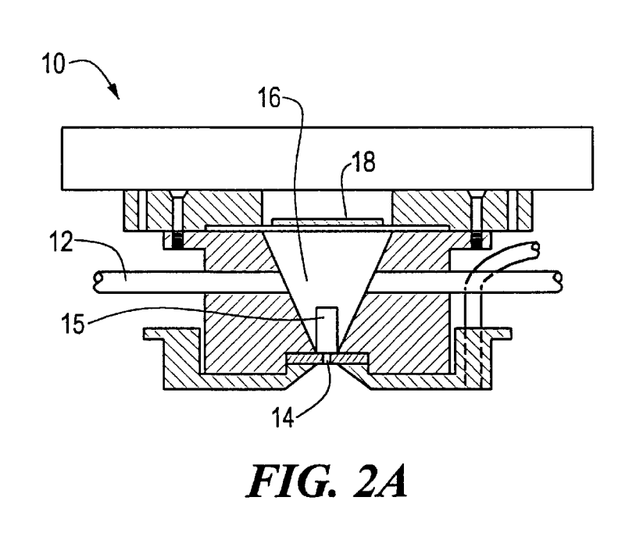
FIG. 2A is a schematic of an acoustically excited aerosol generator used in the process of the present invention.

The liquid feed solution is then conducted into an aerosol generator. An example of a suitable aerosol generator is shown in FIG. 2A. The aerosol generator 10 shown in FIG. 2A was constructed by the inventors. However, other commercially available aerosol generators having a high flowrate and incorporating provisions for droplet size control may be suitable for the practice of the present invention. Alternatively, the aerosol may be a commonly used-spray gun.

The aerosol generator 10 may be adjusted to generate a controlled or uncontrolled size aerosol containing spherical and monodisperse or polydisperse drops, respectively, of the feed solution.

Figure 2B:
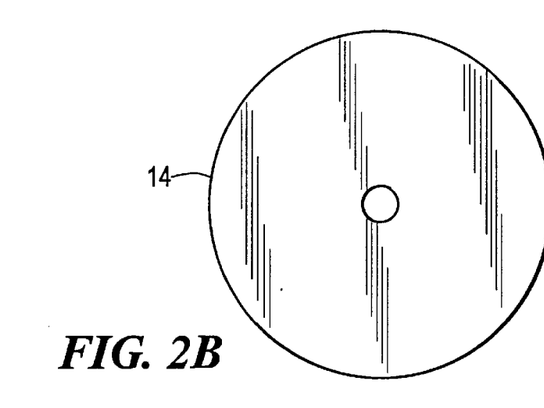
FIG. 2B is an enlarged view of a single-orifice plate which may be used in conjunction with the aerosol generator shown in FIG. 2A.
Figure 2C:
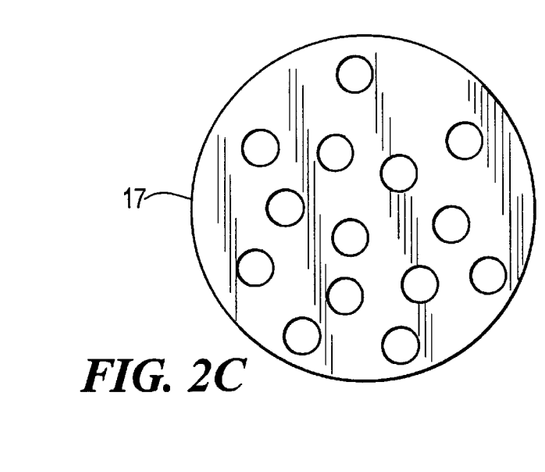
FIG. 2C is an enlarged view of a multi-orifice plate which may be used in conjunction with the aerosol generator shown in FIG. 2A.

In the aerosol generator 10, the liquid feed solution enters through a liquid inlet 12 and the liquid is forced through a small orifice in the orifice plate 14. The orifice plate 14 is shown in greater detail in FIG. 2B. Alternatively, the yield of droplets may be enhanced per unit time by fitting the orifice plate 14 with a multi-orifice plate 17 as shown in FIG. 2C. If monodispersed particles are to be produced, the liquid in the generator's cavity 16 is concurrently oscillated at a high frequency using a peizoelectric transducer 18. The vibration creates an instability which leads to the break-up of the liquid jet into an aerosol comprising uniformly-sized droplets. The size of the droplets may be controlled by the size of the orifice, the oscillator frequency and the liquid feed rate. Thus, the size of the droplets in the aerosol depends on all of the above parameters in addition to the degree of dilution of the polymer (mass fraction of solvent).

The production of polydisperse particles does not usually require controlled aerosol generation or that the liquid jet be vibrated as discussed above for monodisperse particles.

A small tube 15 may be inserted prior to the orifice of the present configuration to prevent plugging by any existing impurities. Also, an optional filter may be used in-line before the generator to further prevent impurities from entering the generator and plugging the orifice.

Figure 3:
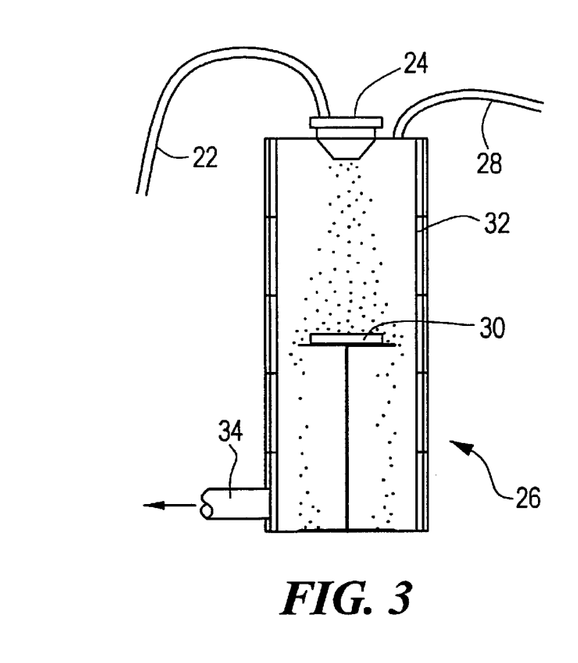
FIG. 3 is a schematic drawing of a thermal reactor used in the process of the present invention.

Referring to FIG. 3, which shows a schematic of the coating process of the invention, it can be seen that droplets of a polymeric solution 22 are formed by atomizer 24 and sprayed into a thermal reactor 26 as an aerosol, along with carrier gas which enters at feed line 28, at the top of the object to be coated 30. The surrounding gas is heated, by heating elements 32, in stages to an optimum temperature. Object 30 is positioned at an optimum and predetermined distance from atomizer 24. Object 30 may move during the coating process (e.g., by rotation, vibration, etc.). Optionally, reactor 26 may be exhausted through exit line 34 and maintained under vacuum during the coating process. The spray may be directed to the top, the bottom or the side of the reactor.

As discussed above, the droplets produced to form a coating on a surface in accordance with the invention may be monodisperse (uniformly sized) or polydisperse (different sizes). Polydisperse particles may be produced by essentially uncontrolled aerosol generation. However, the production of monodisperse particles requires controlled aerosol generation, as is described below.

Monodispersion of the droplets can be accomplished by adjusting the liquid feed flowrate and finely tuning the oscillation frequency. Theoretically, it has been derived elsewhere that the range of lengths of the wavelength for exitation to achieve monodispersivity, $\lambda$, in micrometers is $$3.5 D_j < \lambda < 7 D_j$$

where $\lambda$ is the wavelength of excitation. In practice, fine tuning within this range is required to determine the exact frequency window. Thus, a quartz observation window may be mounted on the top of the thermal reactor to facilitate monitoring of the operation and uniformity of the aerosol and to check for monodispersitivity of the droplets. A small gas jet or test jet may be used in combination with the quartz observation window to visually check for monodispersitivity of the droplets. The test jet impinges perpendicularly to the aerosol jet stream, and droplets of equal size deflect at the same angle while polydisperse droplets deflect at a multitude of angles (satellites). Adjustments to the flow rate and frequency may be made to facilitate monodispersion as discussed above.

Coatings formed by the process of the invention may be designed to exhibit different properties. For example, the strength of adhesion of the coating to the surface; the total surface area of the coating; the percentage of the surface of the object that actually is coated; and the continuity of the coating, which determines the ability of the coating to peel all in one piece all can be varied. The flexibility of the coating is dependent on the last two properties.

In the process of the invention, not all of the solvent in the feed solution needs to evaporate, nor do the droplets need to be at low temperature. Thus, the droplets do not need to be completely solid particles in order to adhere to the surface that is being coated. The temperature at which the process of the invention can be carried out can take any value, commensurate with the other design parameters, to achieve the specific coating properties desired.

The novelty of the present invention rests in the property that when the formed droplets hit the surface to be coated, they are not quite liquid but are not quite dry either. Thus, when the droplets hit the surface, they readily adhere to the surface. They may deflate or they may wrinkle, but they remain more or less discrete particles rather than diffusing and forming a smooth coating.

As a result of these properties, the process of the invention can be used to form multi-layer, hetreogeneous coatings. For example, referring to FIG. 8, a coating can be formed from large spherical particles which are completely dry when they hit the surface to be coated. These particles are then coated with an overcoating consisting of much smaller particles, to keep the large sphere adhered to the surface.

The coating prepared by the process of the invention may or may not cover the entire area exposed to the spray, depending, among other factors, on the exposure time. Furthermore, the coating may be continuous (peel in one piece) or not. Therefore, coatings produced according to the process of the invention can be more flexible and stronger than coatings produced in conventional ways. Also, the surface area of the coating may vary at will, either increase or decrease, which may control the mass diffusion rates through the surface.

In other embodiments, a variety of atomizers can be used to control the droplet size, the spray shape and diameter and, therefore, the uniform application of the coating; the particles in the finished coating may contain gas enclosures (bubbles); other solids may be introduced into the feed solution, which may or may not dissolve in the solvent; monomers can be used instead of polymers (with the polymerization step taking place inside the reactor); and crosslinking and/or foam forming agents, etc., can also be used.

In another embodiment, coatings according to the process of the invention can be prepared on medical devices, e.g., for use in the control of drug delivery rates. The coatings can be tailored at will to accommodate controlled drug releases rate by changing the particle size and the structure of the particle surface.

The following examples are presented to illustrate the advantages of the present invention and to assist one of ordinary skill in making and using the same. These examples are not intended in any way otherwise to limit the scope of the disclosure.

EXAMPLE I

Application of the process of the invention to coat a medical stent

One part of poly(vinyl acetate) (PVA) was dissolved in 10–400 part of acetone. The solution was sprayed in a thermal reactor, as shown in FIG. 3A. The temperature of the feed stream varied within the range of 20–100° C. Nitrogen was used either to assist in the atomization step or as a carrying gas in the reactor. FIGS. 9A–9D show different types of coatings produced on medical stents according to the process of the invention.

EXAMPLE II

Application of the process of the invention to form a series of different coatings on medical stents A total of twelve stents (ten large and two small) and several microscope slides were coated with poly (vinyl acetate) (PVA), according to the process of the invention. Both the inside and the outside surfaces of the stents were coated. The coating process was usually 1-step and the time required varied between 20 seconds and 3 minutes per stent.

Care was taken so that a different type of coating was applied to each stent or slide. The different types of coatings exhibit a variety of properties with respect to the surface area, porosity, flexibility and thickness of the coating, as well as the strength of the bond between the stent and the coating.

Figure 4A:
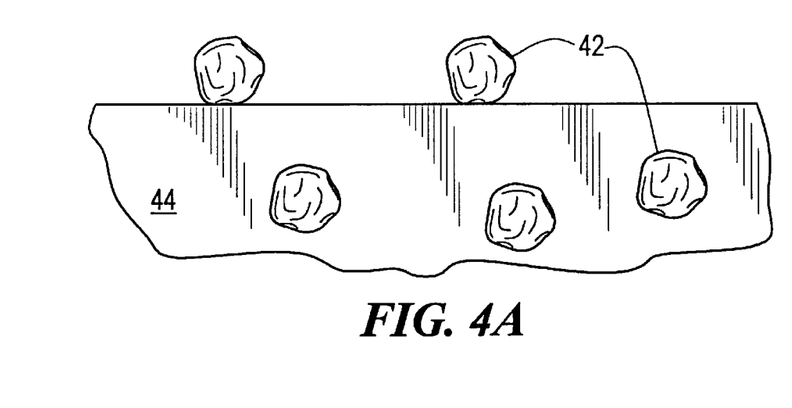
FIG. 4A is a schematic drawing of a coating of the invention consisting of discrete spherical particles (1–100 $\mu$m) attached to a surface.
Figure 4B:
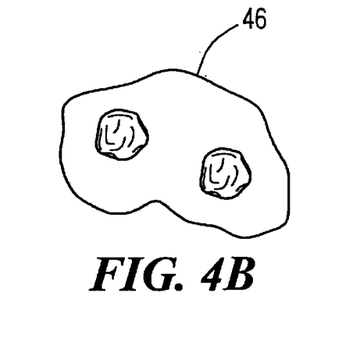
FIGS. 4B, 4C, and 4D are schematic drawings showing coatings consisting of discrete spherical particles (1–100 $\mu$m) attached either directly to a surface, or to polymer membranes. The number of membranes per unit surface area and their size may vary.
Figure 4C:
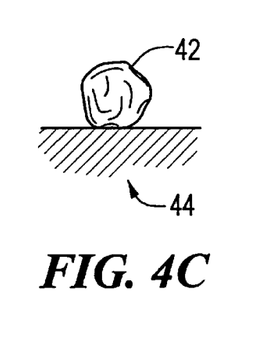
Figure 4D:
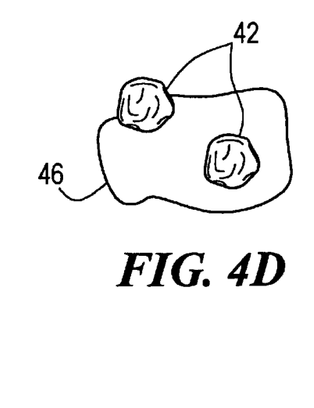
Figure 5:
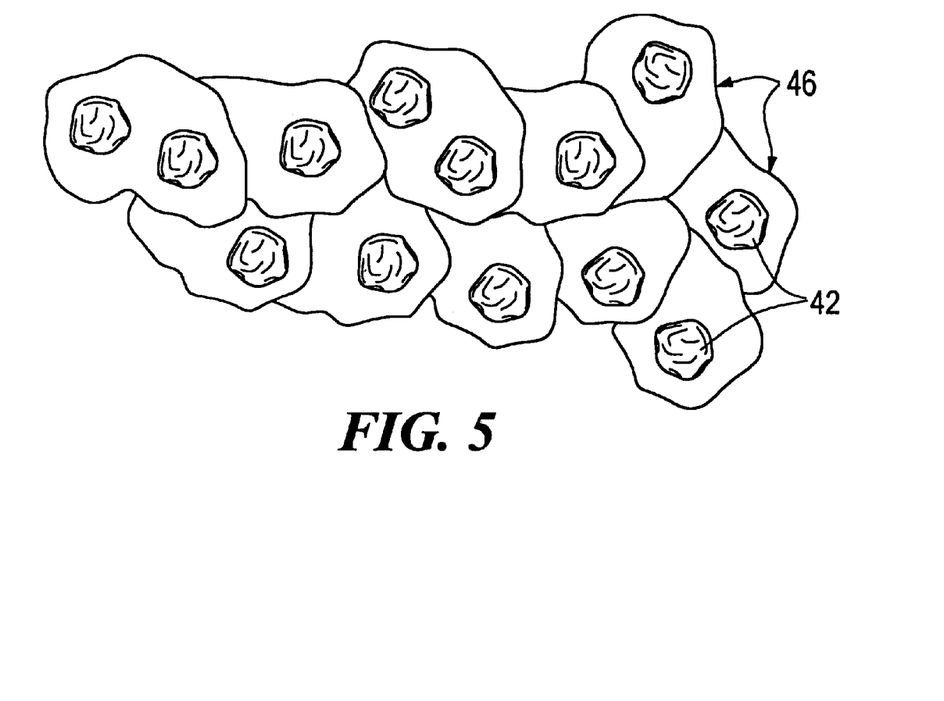
FIG. 5 is a schematic drawing of a coating of the invention consisting of discrete spherical particles (1–100 $\mu$m) attached on polymer membranes.

Referring to FIG. 4A, stent #1 was coated with discrete particles 42 attached to the surface of the stent 44 rather loosely. As indicated in FIG. 4B–4D stents #2–4 were coated with a combination of thin, circular shaped PVA membranes 46 and discrete particles 42. The discrete particles 42 were either strongly attached to membrane 46 or loosely to the metal of the stent 44. Note that for stents 1–4, the whole area of the stent was not covered with coating.

Stent #5 was coated with layers of circular shaped PVA membranes 44, and the discrete particles 42 are strongly attached to the membranes. This coating was so well attached to the stent that it could not be removed when it was scraped with a metal blade.

Figure 6:
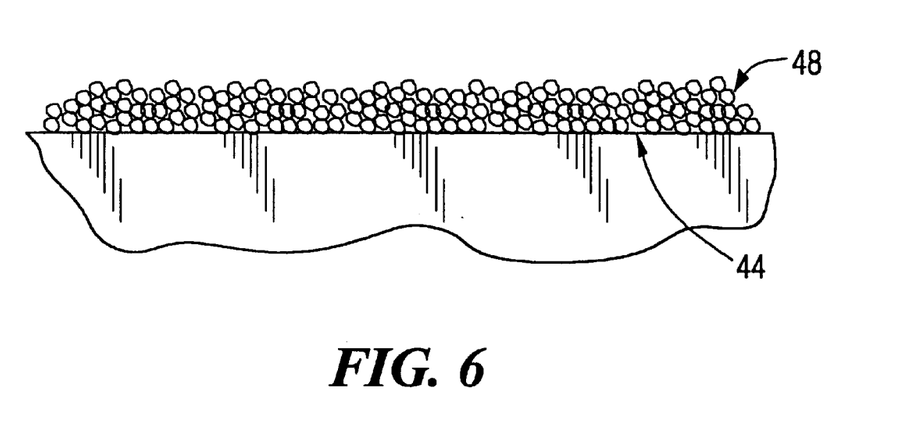
FIG. 6 is a schematic drawing of a coating consisting of small, (1–10 $\mu$m) particles, spherical, spheroidal or of irregular shape particles glued together, forming a coating with a high surface area.
Figure 10A:
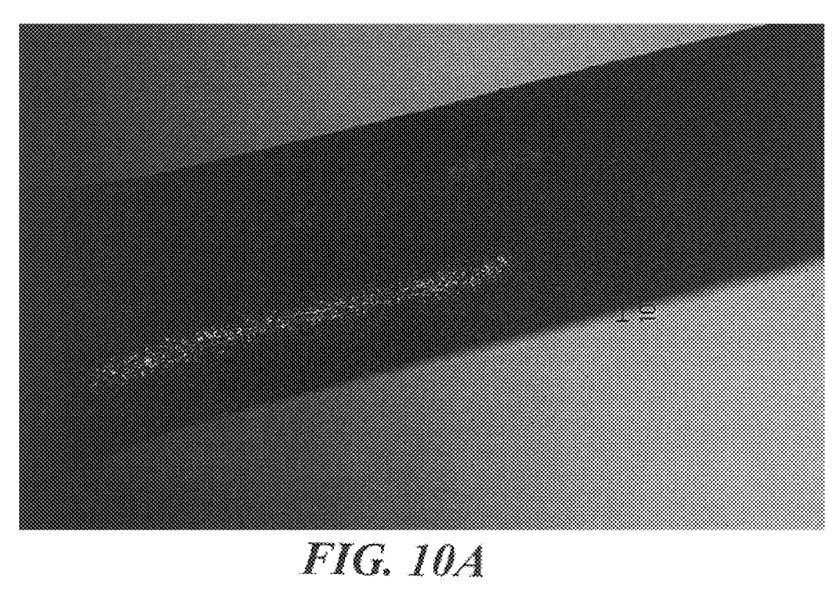
FIGS. 10A and 10B are micrographs, at two different magnifications, of Stent #8, which is covered with layers of particles 1–5 $\mu$m, according to the process of the invention. The particles form a high surface area coating which is strongly attached to the stent.
Figure 10B:
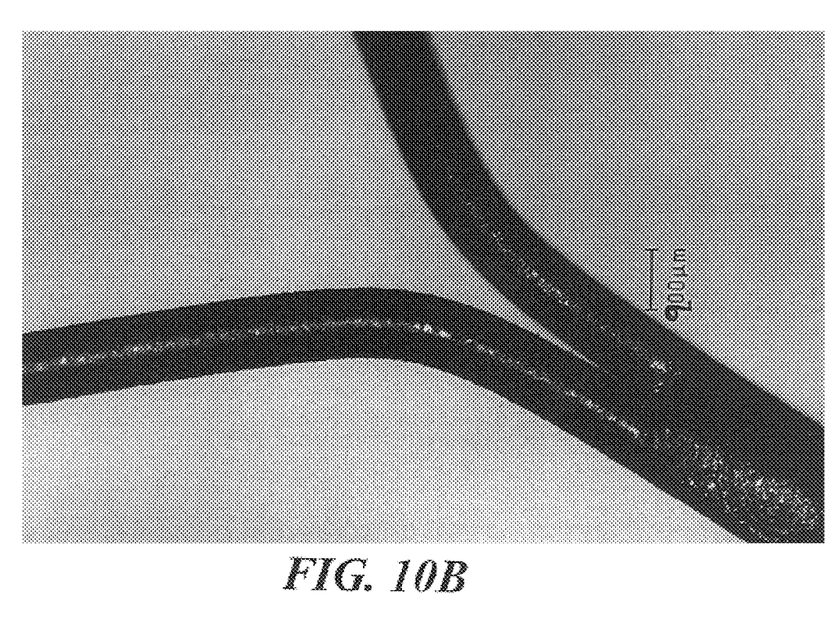

As shown in the schematic of FIG. 6 and the micrographs of FIGS. 10 and 10B, stents #6–8 were coated with layers of very small particles 48, 1–5 μm in diameter, which were strongly attached to the surface of the stent 44. The difference between these stents is the thickness of the coating, with the coating on stent #8 being the thickest. This type of coating seems to be continuous and porous with high surface area, and it covers most or all the surface of the stent.

Figure 11A:
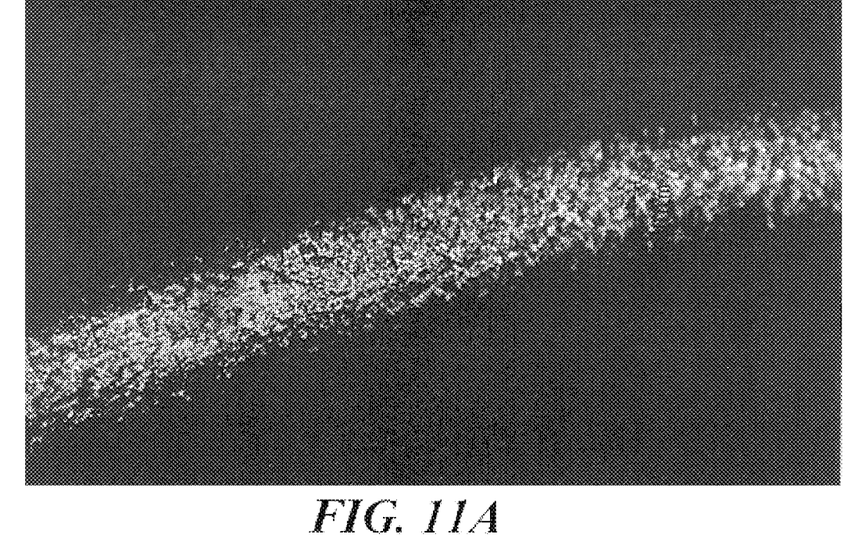
FIGS. 11A and 11B are micrographs, at two different magnifications, of Stent #9, which is coated with PVA mixed with red food coloring, according to the process of the invention.
Figure 11B:
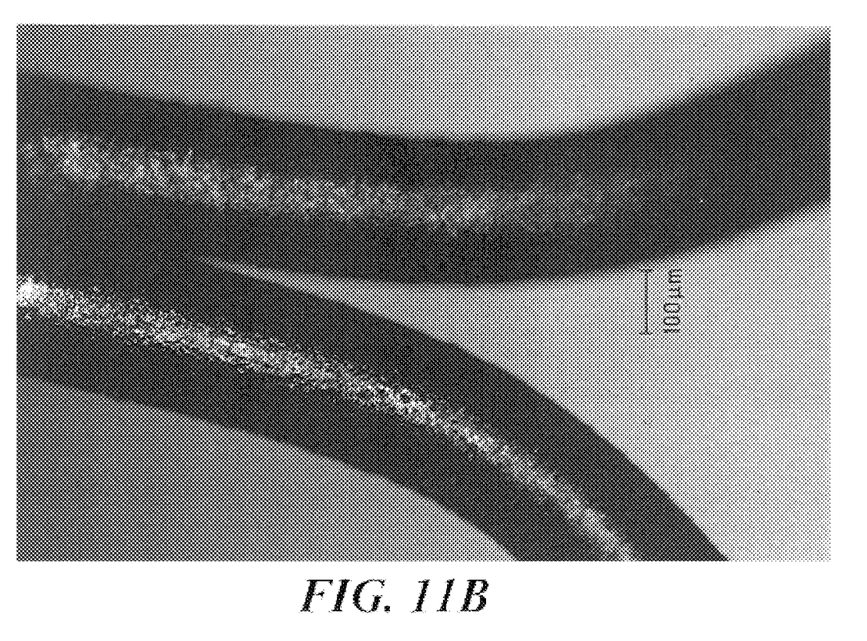

Stent #9 was coated with layers of very small PVA particles mixed with food coloring, as shown in the micrographs of FIGS. 11A and 11B. The idea behind this test was to use the food coloring to simulate an added drug.

Figure 7:
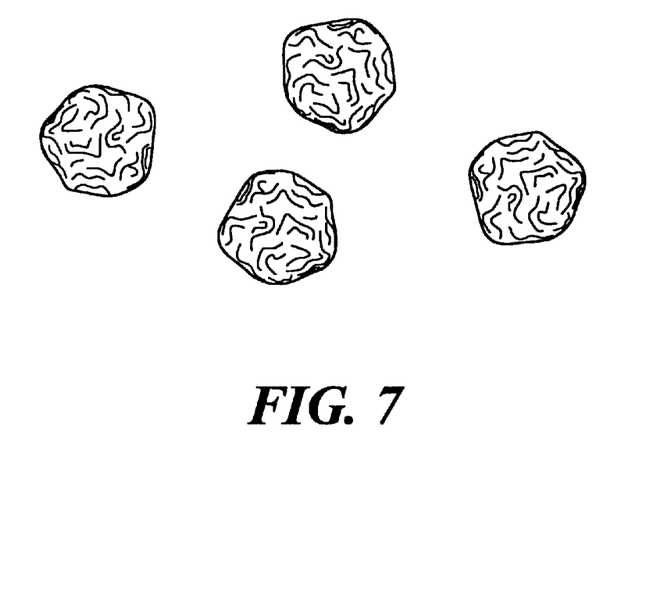
FIG. 7 is a schematic drawing of a coating consisting of collapsed particles with wrinkled surfaces attached to a coated surface.
Figure 12A:
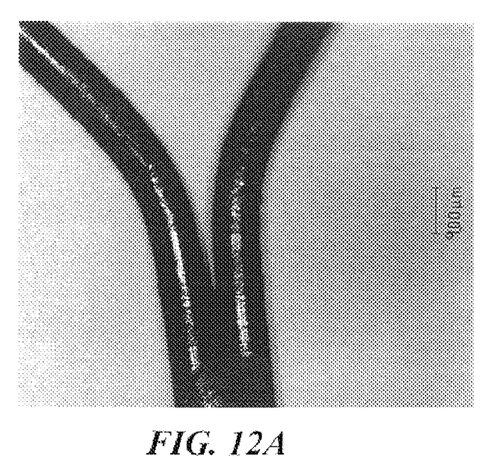
FIGS. 12A and 12B are micrographs, at two different magnifications, of Stent #10, which is coated with collapsed particles, strongly attached to the surface of the stent, according to the process of the invention.
Figure 12B:
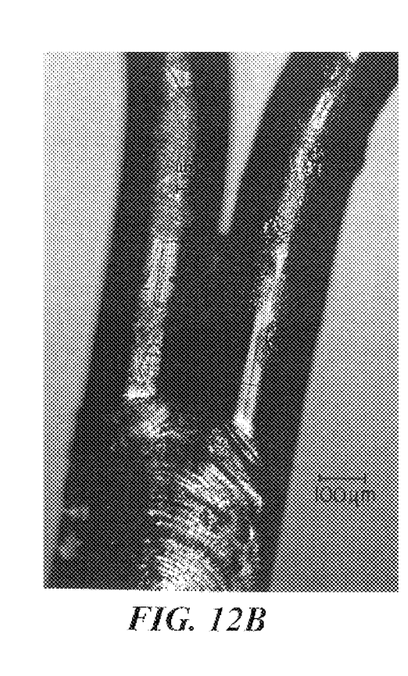

Stent #10 was coated with discrete and deflated spheres, as shown in the schematic of FIG. 7 and micrographs of stent #10, FIGS. 12A and 12B. These particles are very well attached to the surface of the stent and they seem to have high surface area. Note that if the stent is exposed to the spray for a longer period of time, the particles will no longer be discrete, but rather form a continuous coating.

Figure 13A:
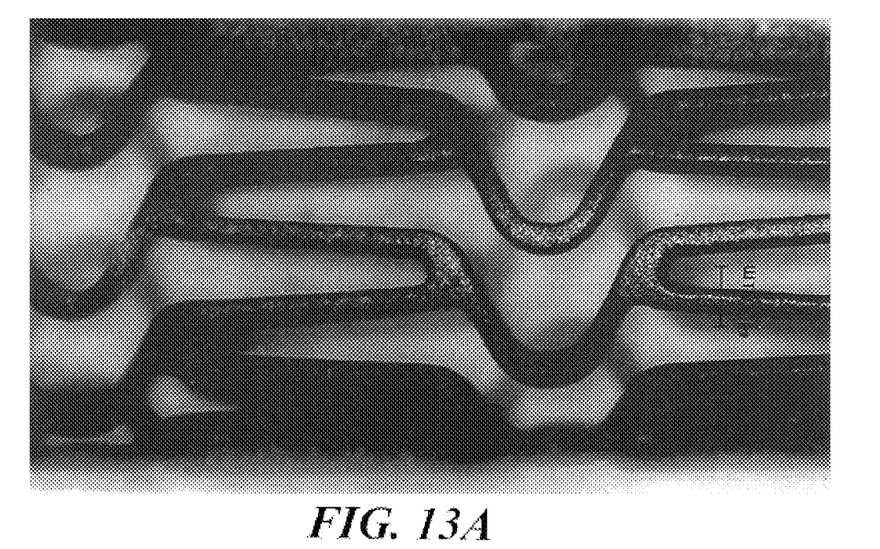
FIGS. 13A and 13B are micrographs, at two magnifications, of Stent #12, which is uniformly covered with 1–5 μm particles, strongly attached to the surface according to the process of the invention.
Figure 13B:
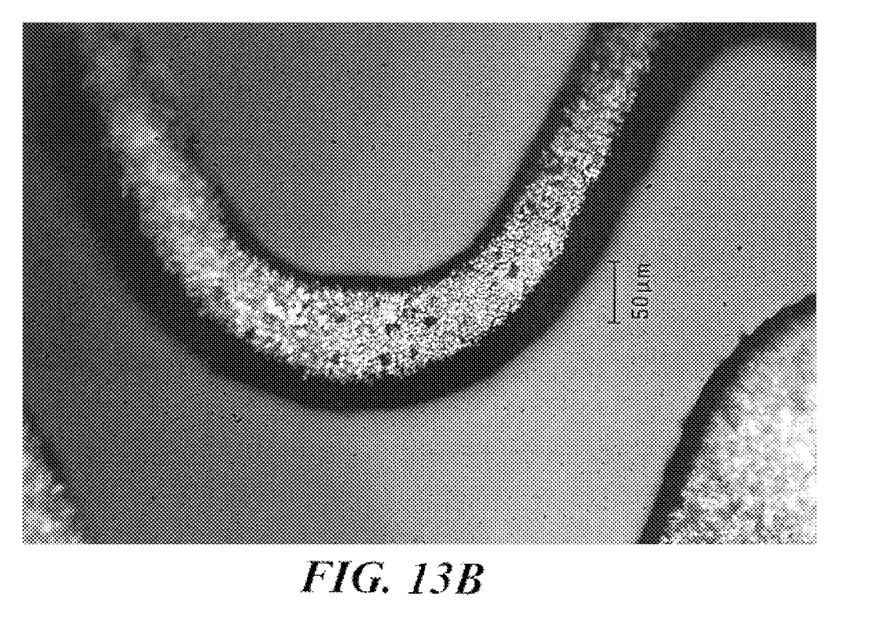

Stent #11 (the small stent) was coated with layers of 1–5 μm particles. Stent #12 is similar to stent #11, with a thicker coating as shown in the pictures of stent #12, FIGS. 13A and 13B. Accumulation of excess material in the crevices of the stent was not observed and the coating looked uniform.

Figure 14:
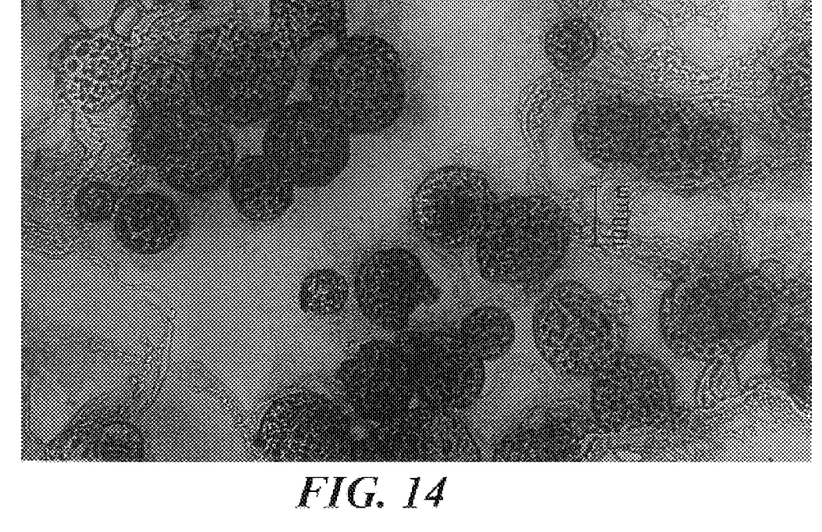
FIG. 14 is a micrograph of a glass slide, coated according to the process of the invention, wherein the coating consists of collapsed spheres.

Slide #1A (FIG. 14) was coated mostly with collapsed spheres with wrinkled surface, which seem to have a high surface area See also the schematic of FIG. 7.

Figure 8:
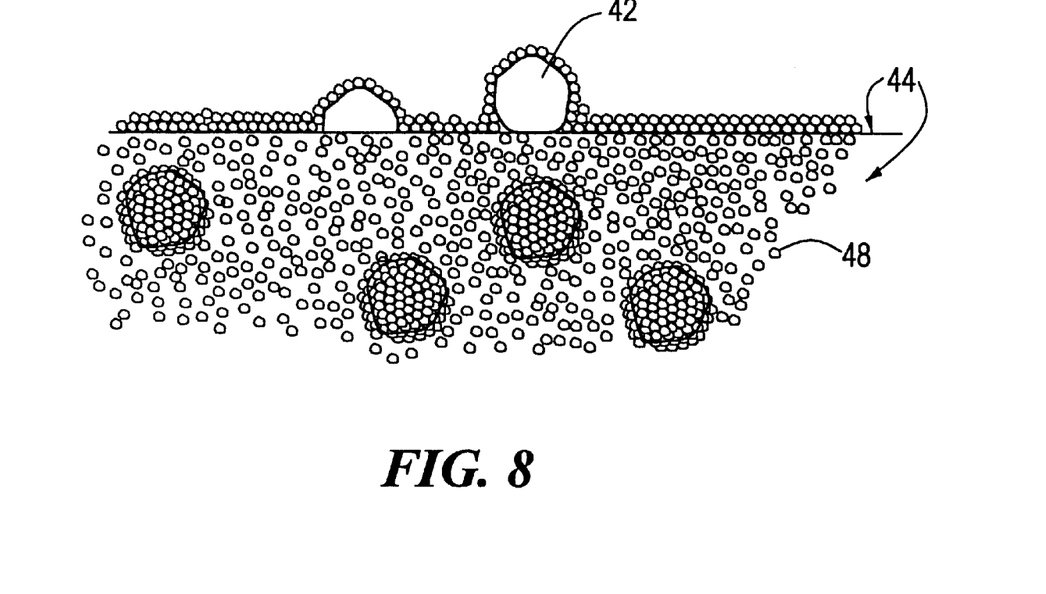
FIG. 8 is a schematic drawing of a coating consisting of discrete spherical particles (1–100 $\mu$m) attached to the surface. An additional coating has been superimposed, as depicted in FIG. 6.
Figure 9A:
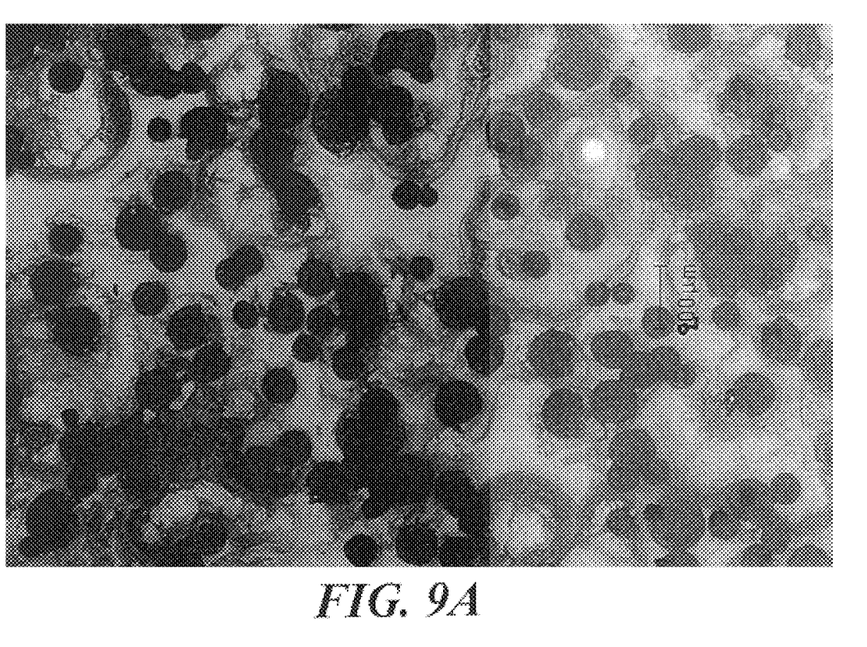
FIG. 9A is a micrograph of a glass slide, coated according to the process of the invention as shown in FIG. 5.
Figure 9B:
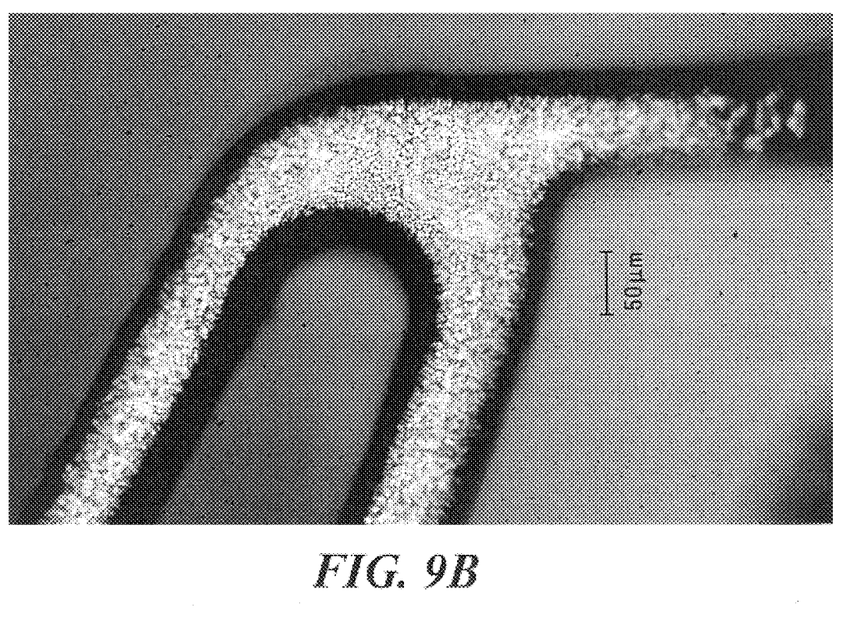
FIG. 9B is a micrograph of a medical device, e.g., a stent, coated according to the process of the invention as shown in FIG. 6.
Figure 9C:
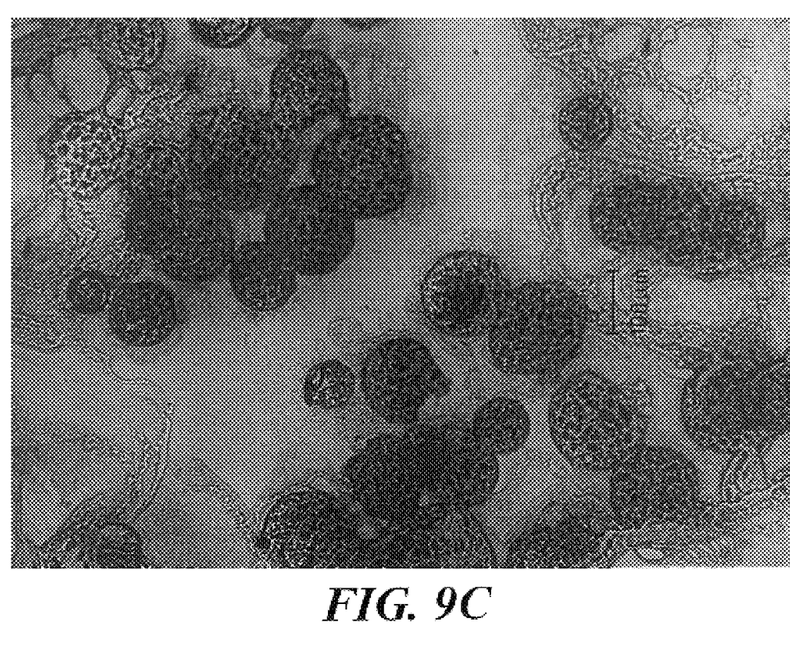
FIG. 9C is a micrograph of a glass slide, coated according to the process of the invention, wherein the coating consists of collapsed spheres as shown in FIG. 7.
Figure 9D:
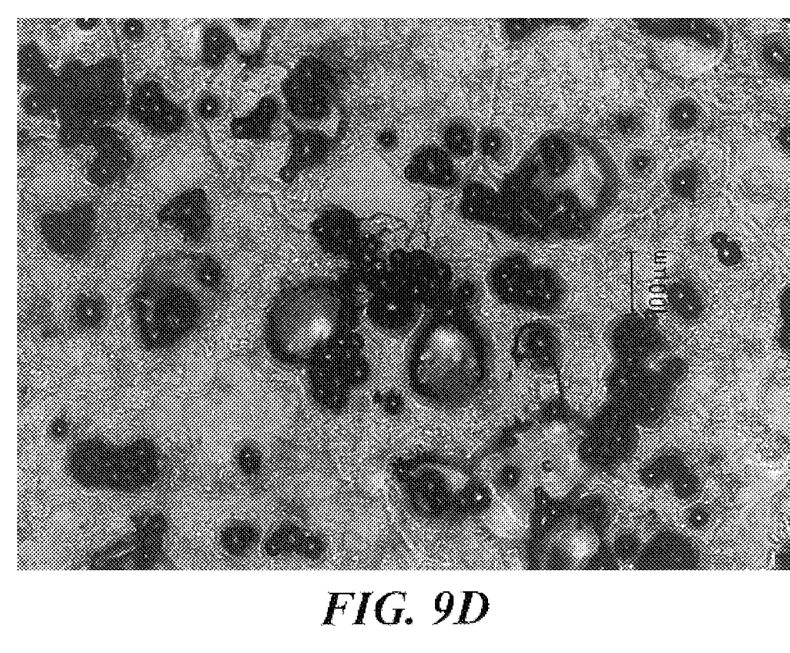
FIG. 9D is a micrograph of a glass slide, coated according to the process of the invention, wherein the coating consists of discrete large spheres (50–70 $\mu$m) covered by tiny spheres attached to each other as shown in FIG. 8.

Slide #1B (FIG. 15) was coated, as shown in the schematic of FIG.8, with both large discrete particles 42, 50–75 μm in diameter, and small particles 48, 1–5 μm, which keep the large particles strongly attached to the surface of the stent 44.

Figure 15:
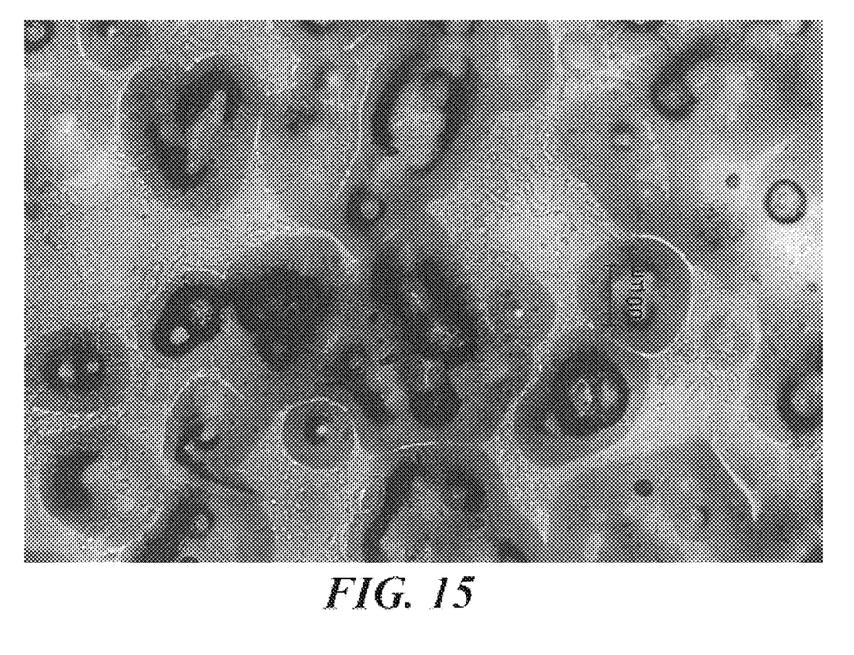
FIG. 15 is a micrograph of a glass slide, coated according to the process of the invention, wherein the coating consists of discrete particles (50–75 μm) covered by layers of 1–5 μm particles attached to each other.

Thus, the coatings consisted of:

(a) discrete particles (20–100 μm) or membranes as is the case with the stents #1–4, 10 and slide 1A (FIG. 14), or (b) continuous layers of tiny particles (1–5 μm) as is the case with stents #6–9 and 11–12, or (c) a combination of discrete particles, membranes and layers of tiny particles as is the case with stent #5 and slide 1B (FIG. 15).

The percentage of coverage of the surface was variable at will, from a total coverage of 100% to any other number less than that. The various parameters of the spray were controlled so as to achieve a uniform coating and avoid the excess material in the crevices of the stent, see stents #6–12.

The surface area of the coating was controlled by the following mechanisms:

(a) by coating the stent with discrete particles with smooth surface, 10–100 μm in diameter, see stents #1–5, (b) by coating the stent with collapsed and wrinkled particles, see stent #10 and slide 1A (FIG. 14), (c) by coating the stent with continuous layers of tiny particles, see stents #6–9 and 11–12. The voids between the particles may form a network of pores, potentially resulting in the increase of surface area by orders of magnitude.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method for producing a porous polymer coating on a surface comprising the steps of:

preparing a liquid feed solution comprising polymer, or monomer and polymerization catalyst in a solvent;

conducting said liquid feed solution into an aerosol generator;

generating an aerosol in the form of droplets;

spraying said aerosol into a thermal reactor onto the surface of an object;

regulating the temperature and pressure of said thermal reactor during said spraying step so that a portion, but not all, of said solvent in said feed solution evaporates before partially evaporated droplets of said aerosol are deposited onto said surface; and maintaining said aerosol in said thermal reactor for a period of time sufficient to allow an adherent, porous polymer coating to form on said surface.

2. The method of claim 1, wherein in said generating step, said aerosol generation is controlled and said droplets are monodisperse.

3. The method of claim 1, wherein in said generating step, said aerosol generation is uncontrolled and said droplets are polydisperse.

4. The method of claim 1, wherein said monomer comprises any liquid monomer or mixtures of monomers whose polymerization in bulk can be readily controlled.

5. The method of claim 4, wherein said monomers are styrene, methyl methacrylate, acrylic acids, vinyl acetate, divinyl acetate, divinyl benzene, or mixtures thereof.

6. The method of claim 1, wherein said polymerization catalyst is benzoyl peroxide or potassium persulfate.

7. The method of claim 1, wherein said solvent is toluene, acetone, benzene, butanone, water, methanol, ethanol or hexane.

8. The method of claim 1 wherein, in said preparing step, said liquid feed solution further comprises a component to be deposited on said surface in said coating.

9. The method of claim 8 wherein said component is selected from the group consisting of a salt, a drug, and carbon black.

10. The method of claim 2, wherein said conducting step includes forcing said liquid feed solution through a small orifice in said aerosol generator while simultaneously oscillating said feed solution at a predetermined high frequency and maintaining a predetermined liquid feed rate and polymer dilution rate.

11. The method of claim 10, wherein in said generating step, the monodispersitivity and size of said droplets is controlled by adjusting the size of said orifice, the frequency of the oscillation, the liquid feed rate, and the polymer to solvent dilution ratio.

12. The method of claim 1, wherein said thermal reactor is an externally heated thermal reactor having at least one stage.

13. The method of claim 11, wherein said thermal reactor is capable of being heated to a predetermined temperature profile.

14. The method of claim 2, wherein said thermal reactor further comprises a quartz observation window to facilitate monitoring the monodispersitivity of the droplets in said aerosol jet.

15. The method of claim 1, wherein said polymer is any polymer that can be completely dissolved in a solvent.

16. The method of claim 1, wherein said polymer is poly(styrene), poly(methyl-methacrylate), poly(methylethacrylate) acrylic resins, poly(-vinyl-acetate), poly(butadiene), poly(esters) (uncross-linked), formaldehyde resins, gelatins, proteins, poly-(ethylene-terephthalate) or poly(vinyl-chloride).

* * * * *

UNITED STATES PATENT AND TRADEMARK OFFICE
CERTIFICATE OF CORRECTION

PATENT NO. : 6,143,370
DATED : November 7, 2000
INVENTOR(S) : Thomai Panagiotou et al.

It is certified that error appears in the above-identified patent and that said Letters Patent is hereby corrected as shown below:

Column 6,
Line 59, "area See" should read -- area. See --.

Signed and Sealed this

Thirtieth Day of July, 2002

Attest:

Attesting Officer

JAMES E. ROGAN
Director of the United States Patent and Trademark Office